(12) United States Patent
Bedingham et al.

(10) Patent No.: US 6,532,997 B1
(45) Date of Patent: Mar. 18, 2003

(54) SAMPLE PROCESSING DEVICE WITH INTEGRAL ELECTROPHORESIS CHANNELS

(75) Inventors: William Bedingham, Woodbury, MN (US); Raj Rajagopal, Woodbury, MN (US); Kannan Seshadri, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/034,334

(22) Filed: Dec. 28, 2001

(51) Int. Cl.[7] .............................................. G01N 27/00
(52) U.S. Cl. ........................ 141/1; 141/34; 204/451; 204/601
(58) Field of Search ................... 141/1, 34; 204/451, 204/601

(56) References Cited

U.S. PATENT DOCUMENTS

| | | | |
|---|---|---|---|
| 4,708,782 A | * 11/1987 | Andresen et al. | ........ 210/198.2 |
| 5,126,022 A | 6/1992 | Soane et al. | |
| 5,750,015 A | 5/1998 | Soane et al. | |
| 6,017,765 A | * 1/2000 | Yamada et al. | ........... 623/1.15 |
| 6,068,751 A | 5/2000 | Nuekermans | |
| 6,143,152 A | 11/2000 | Simpson et al. | ........... 204/451 |
| 6,302,134 B1 | 8/2001 | Kellogg et al. | |
| 6,284,113 B1 | 9/2001 | Bjornson et al. | |
| 6,303,343 B1 | 10/2001 | Kopf-Sill | |
| 6,306,273 B1 | 10/2001 | Wainright et al. | |
| 6,319,469 B1 | 11/2001 | Mian et al. | ................... 422/64 |

FOREIGN PATENT DOCUMENTS

| | | |
|---|---|---|
| WO | WO 98/22625 A1 | 5/1998 |
| WO | WO 00/17624 A2 | 3/2000 |
| WO | WO 00/45180 A1 | 8/2000 |
| WO | WO 00/62931 A1 | 10/2000 |
| WO | WO 00/68336 A1 | 11/2000 |
| WO | WO 01/02737 A1 | 1/2001 |
| WO | WO 01/25137 A1 | 4/2001 |
| WO | WO 01/25138 A1 | 4/2001 |
| WO | WO 01/27253 A1 | 4/2001 |
| WO | WO 01/30995 A1 * | 5/2001 |
| WO | WO 01/31322 A1 | 5/2001 |
| WO | WO 01/47637 A1 * | 7/2001 |
| WO | WO 01/47638 A2 | 7/2001 |
| WO | WO 01/54810 A1 | 8/2001 |
| WO | WO 01/86249 A1 * | 11/2001 |

OTHER PUBLICATIONS

NIST Grant, Project Brief [online], "Tools for DNA Diagnostics (Oct. 1998) Integrated, Micro–Sample Preparation System for Genetic Analysis," [retrieved on Aug. 5, 2002] 2 pgs. Retrieved from the internet at <http://jazz.nist.gov/atpcf/prjbriefs.cfm?Product No.=98–08–0031>.*

Scherer et al., "High–Pressure Gel Loader for Capillary Array Electrophoresis Microchannel Plates," Biotechniques, vol. 31; No. 5; pp. 1150–1154 (Nov., 2001).*

US 2002–0047003–A1; Apr. 25, 2002; Bedingham et al.
US 2002–0048533–A1; Apr. 25, 2002; Harms et al.
US 2002–0064885–A1; May 30, 2002; Bedingham et al.

* cited by examiner

Primary Examiner—J. Casimer Jacyna
(74) Attorney, Agent, or Firm—Christopher D. Gram; Robert W. Sprague

(57) ABSTRACT

Sample processing devices with electrophoresis channels and methods of loading the electrophoresis channels with electrophoresis sieving polymer while rotating the sample processing device are disclosed. In some instances, the electrophoresis channels may be arranged radially relative to the axis of rotation of the sample processing device. In other sample processing devices, the electrophoresis channels may be arranged in curved arcs that are concentric about the center of the sample processing device (which preferably corresponds to the axis of rotation).

16 Claims, 5 Drawing Sheets

SAMPLE PROCESSING DEVICE WITH INTEGRAL ELECTROPHORESIS CHANNELS

GRANT INFORMATION

The present invention may have been made with support from the U.S. Government under NIST Grant No. 70NANB8H4002. The U.S. Government may have certain rights to the inventions recited herein.

FIELD OF THE INVENTION

The present invention relates to the field of sample processing devices and methods. More particularly, the present invention relates to sample processing devices with integral electrophoresis channels and methods of loading the electrophoresis channels with an electrophoresis sieving polymer.

BACKGROUND

The preparation of a biological sample for, e.g., DNA sequencing and detection can involve a number of critical processes and transfers. For example, a user may be required to prepare a biological sample input (e.g., purified DNA target, whole blood/tissue, etc.) and extraction/clean-up. After these steps are completed, the sample materials may typically undergo polymerase chain reaction (PCR) amplification, clean-up and possible detection. The prepared PCR amplification products may then undergo Sanger amplification and clean-up. Following these steps, the end product of the processed sample material may undergo electrophoresis and fluorescence detection.

Each of these procedures can require considerable human intervention and a number of fluid transfers, all of which can result in errors, contamination, and exposure to potential biohazards. Furthermore, the time required from sample input to sequence data output can, in some instances be up to 24 hours or more. In addition, the various equipment required to perform the different procedures may cost, e.g., US$100,000 to about US$200,000 or more, thereby increasing the cost of the processing. Further, the personnel performing these procedures are typically highly-skilled, with expertise in DNA sample preparation, machine interface/maintenance, analysis and quality control.

Furthermore, it is important that electrophoresis sieving polymer located along an electrophoresis path, e.g., a capillary or slab, be substantially, if not completely, free of voids and/or bubbles to allow for accurate separation of the analyte. Many different techniques have been developed for loading electrophoresis sieving polymer into capillaries and other electrophoresis devices. Many of these techniques, however, do not allow for the removal of voids and/or bubbles after they are located within the electrophoresis sieving polymer, requiring complete removal of the electrophoresis sieving polymer and reloading or simply discarding the device and beginning with a new device.

SUMMARY OF THE INVENTION

The present invention provides a sample processing device with electrophoresis channels and methods of loading the electrophoresis channels with electrophoresis sieving polymer while rotating the sample processing device.

The sample processing devices are designed for processing sample materials that include chemical and/or biological mixtures. If the sample materials include a biological mixture, the biological mixture preferably includes biological material such as peptide- and/or nucleotide-containing material. It may further be preferred that the biological mixture include a nucleic acid amplification reaction mixture (e.g., a PCR reaction mixture or a nucleic acid sequencing reaction mixture).

In some instances, the electrophoresis channels may be arranged radially relative to the axis of rotation of the sample processing device. In other sample processing devices, the electrophoresis channels may be arranged in curved arcs that are concentric about the center of the sample processing device (which preferably corresponds to the axis of rotation).

Further, the electrophoresis channels may in some instances be unvented, such that the only opening into or out of the electrophoresis channel is located proximate the chamber or port into which the electrophoresis sieving polymer or other sample materials are introduced. In an unvented electrophoresis channel, the terminal end of the electrophoresis channel, i.e., the end distal from the axis of rotation and/or the loading chamber, is sealed to prevent the exit of fluids from the electrophoresis channel.

Sample processing devices in which the electrophoresis channels are vented proximate their terminal ends may preferably include a flow restrictor along the path followed by the electrophoresis sieving polymer during loading of the electrophoresis channel. The flow restrictor may be, e.g., a closed valve that prevents fluid flow until opened, or it may be in the form of a constricted passage through which the electrophoresis sieving polymer must travel during loading.

Regardless of whether the sample processing devices include a valve or a constricted passage, rotation of the sample processing device with the electrophoresis sieving polymer located therein for delivery to the electrophoresis channels provides a significant advantage in that the fluid pressure generated in the electrophoresis sieving polymer during rotation before the electrophoresis sieving polymer passes through the flow restrictor (e.g., while the valve is closed) substantially, if not completely, removes any bubbles sufficiently large to adversely affect the separation to be performed in the electrophoresis channel.

Another advantage of sample processing devices according to the present invention is that even if bubbles or voids are located in the electrophoresis channels after loading with electrophoresis sieving polymer, the bubbles or voids may be removed by further rotation of the sample processing device. In other words, what could be considered a failure during loading can be corrected by additional rotation of the sample processing device (in contrast to the known methods and devices in which the electrophoresis channel must be emptied and reloaded or simply discarded).

In one aspect, the present invention includes a method of providing an electrophoresis channel containing an electrophoresis sieving polymer by providing a device having a plurality of electrophoresis channels and at least one electrophoresis medium chamber; providing electrophoresis sieving polymer in the at least one electrophoresis medium chamber; and rotating the device about an axis of rotation while the at least one electrophoresis medium chamber is in fluid communication with each electrophoresis channel of the plurality of electrophoresis channels, wherein the at least one electrophoresis medium chamber is located radially inward from the plurality of electrophoresis channels relative to the axis of rotation. During rotation of the device, the electrophoresis sieving polymer in the at least one electrophoresis medium chamber moves into the plurality of electrophoresis channels.

In another aspect, the present invention includes a method of providing an electrophoresis channel containing an electrophoresis sieving polymer by providing a device with at least one electrophoresis medium chamber and a plurality of electrophoresis channels, wherein each electrophoresis channel of the plurality of electrophoresis channels is an unvented electrophoresis channel. The method also includes providing electrophoresis sieving polymer in the at least one electrophoresis medium chamber; and rotating the device about an axis of rotation while the at least one electrophoresis medium chamber is in fluid communication with each electrophoresis channel of the plurality of electrophoresis channels, wherein the at least one electrophoresis medium chamber is located radially inward from the plurality of electrophoresis channels relative to the axis of rotation. During rotation of the device, the electrophoresis sieving polymer in the at least one electrophoresis medium chamber moves into the plurality of electrophoresis channels.

In another aspect, the present invention provides a device for processing sample material, the device including a substrate with first and second major surfaces and a hub defining an axis of rotation for the substrate; a plurality of electrophoresis channels in the device, wherein the plurality of electrophoresis channels extend generally radially outward relative to the axis of rotation; a plurality of process chambers in the device, each of the process chambers defining a volume for containing sample material. The device further includes a connection structure located between at least one electrophoresis channel of the plurality of electrophoresis channels and at least one process chamber of the plurality of process chambers, wherein the connection structure has a closed configuration in which sample material is prevented from moving into the at least one electrophoresis channel from the at least one process chamber, and wherein the connection structure has an open configuration in which sample material is capable of moving into the at least one electrophoresis channel from the at least one process chamber. Also included in the device is at least one electrophoresis medium chamber in fluid communication with each electrophoresis channel of the plurality of electrophoresis channels.

These and other features and advantages of the invention may be described in connection with various illustrative embodiments of the invention below.

DETAILED DESCRIPTION OF ILLUSTRATIVE EMBODIMENTS OF THE INVENTION

The present invention provides sample processing devices including integral electrophoresis channels and methods of using the same. The electrophoresis channels may be arranged on the sample processing device in any desired relationship such that rotation of the sample processing device can be used to load the electrophoresis channels with electrophoresis sieving polymers. Different illustrative designs of sample processing devices are depicted in the figures and described herein, although it should be understood that alternative arrangements of electrophoresis channels may be provided in sample processing devices according to the present invention.

Figure 1:
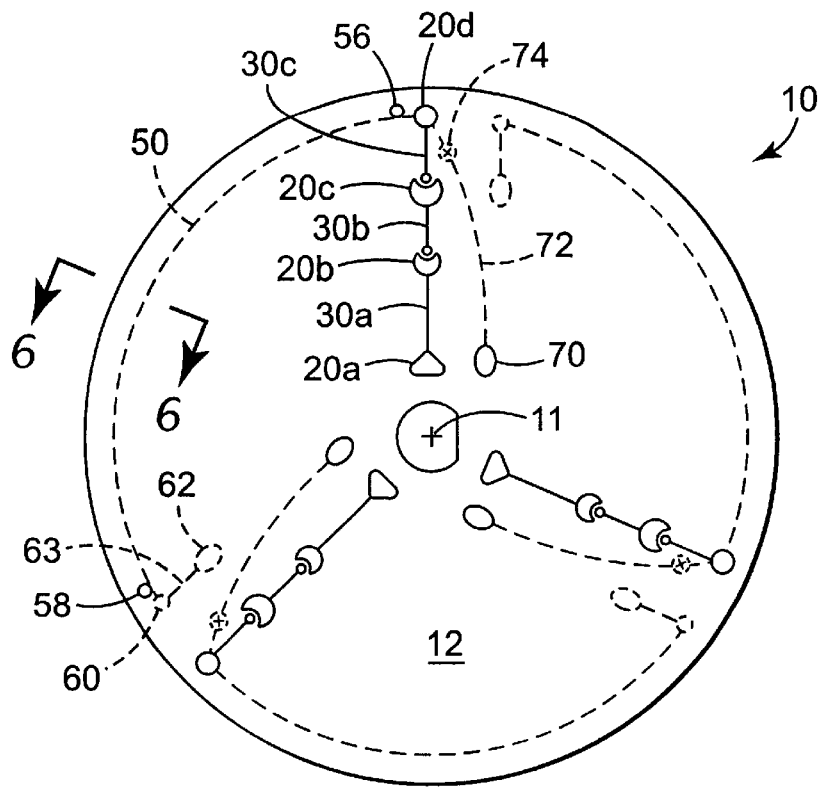
FIG. 1 is a plan view of one sample processing device with integral electrophoresis channels.
Figure 2:
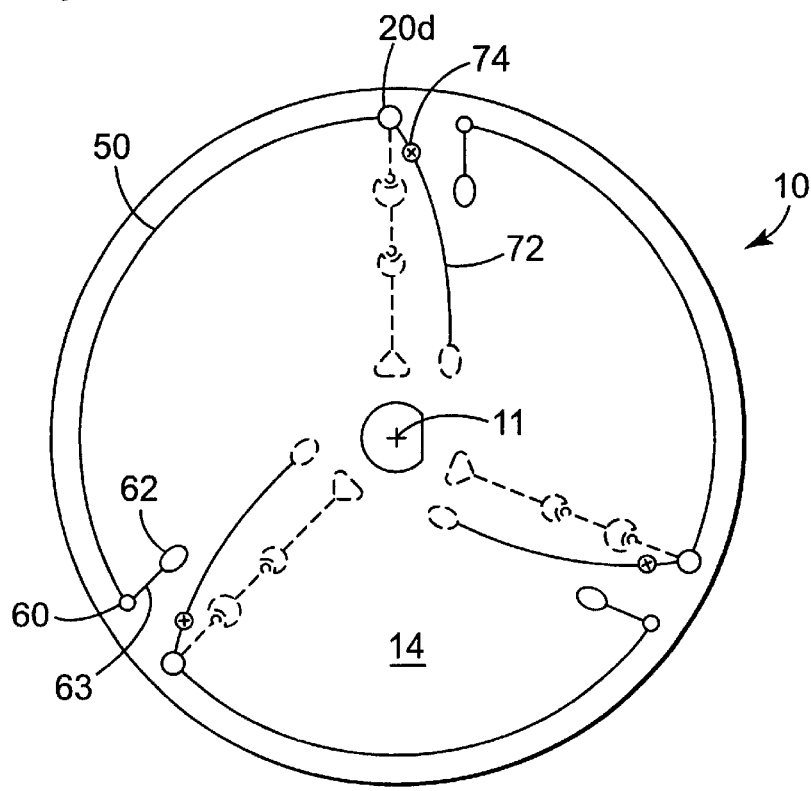
FIG. 2 is a plan view of the opposing side of the sample processing device of FIG. 1.
Figure 3:
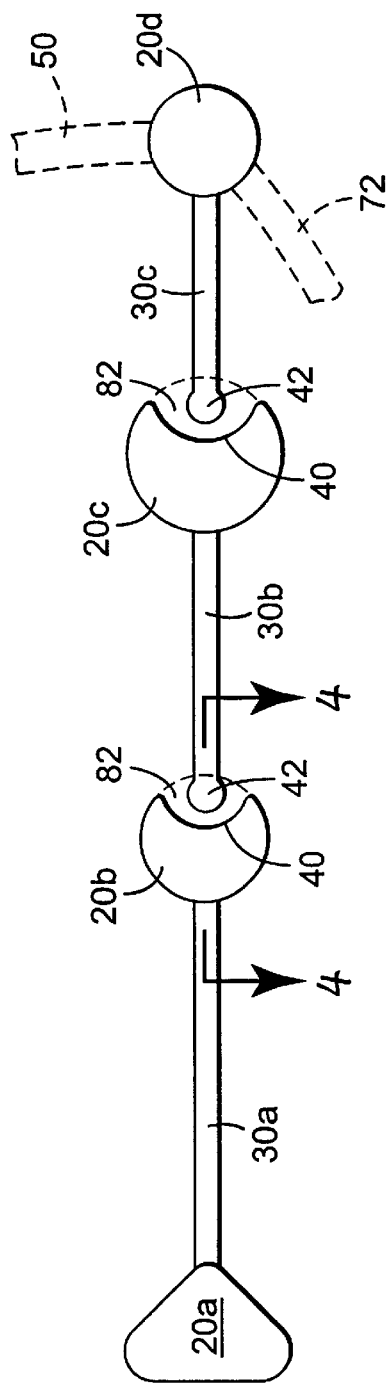
FIG. 3 is an enlarged view of a portion of one process array on the sample processing device of FIG. 1.

One side of one embodiment of a sample processing device 10 is depicted in FIG. 1. The depicted sample processing device has a generally flat, disc-like shape, with two major sides 12 and 14 (with side 12 seen in FIG. 1 and side 14 seen in FIG. 2). The thickness of the sample processing device 10 may vary depending on a variety of factors (e.g., the size of the features on the sample processing device, etc.). In FIGS. 1–3, the features depicted in solid lines are formed on or into the visible side of the sample processing device 10, while the features in broken lines are formed on or into the hidden or opposing side of the sample processing device 10. It will be understood that the exact construction and location of the various features may change in different sample processing devices.

Although relative positional terms such as "top" and "bottom" may be used in connection with the present invention, it should be understood that those terms are used in their relative sense only. For example, when used in connection with the devices of the present invention, "top" and "bottom" are used to signify opposing sides of the devices. In actual use, elements described as "top" or "bottom" may be found in any orientation or location and should not be considered as limiting the methods, systems, and devices to any particular orientation or location. For example, the top surface of the device may actually be located below the bottom surface of the device in use (although it would still be found on the opposite side of the device from the bottom surface).

The sample processing device 10 includes three process arrays, with each of the process arrays including a plurality of process chambers 20a, 20b, 20c, and 20d (referred to collectively as process chambers 20 below). One of the process arrays is enlarged in FIG. 3 to facilitate an understanding of the present invention.

As used in connection with the present invention, the term "process array" is used to refer to a collection of process chambers connected by a passageway such that materials can be transferred between the process chambers. Although the depicted process arrays in FIGS. 1–3 include four process chambers, a process array may include as few as two connected process chambers.

Further, the term "process chamber" should not be construed as limiting the chamber to one in which a process (e.g., PCR, Sanger sequencing, etc.) is performed. Rather, a process chamber as used herein may include, e.g., a chamber in which materials are loaded for subsequent delivery to another process chamber as the sample processing device if rotated, a chamber in which the product of a process is collected, a chamber in which materials are filtered, etc.

The process arrays in sample processing devices of the present invention are arranged such that rotation of the sample processing devices facilitates the transfer of materials within the process arrays. It may be preferred that the process chambers 20 be arranged in a generally radial manner as seen in FIG. 1, such that as the sample processing device 10 is rotated about a central axis of rotation 11, sample materials in the process arrays are driven in the direction of the outermost process chamber 20*d*. In many instances, the innermost process chamber 20*a* may be referred to as a loading chamber, i.e., a chamber into which sample materials may be first introduced into the process array.

Although each of the process arrays of sample processing device 10 is depicted as being independent of the other process arrays (i.e., not in fluid communication with the other process arrays), it should be understood that one loading chamber may be used to supply process chambers in two or more process arrays. In such an instance, the process arrays may be fed by what can be referred to as a common loading chamber.

The process chambers 20 in each process array are sequentially connected by distribution channels 30*a*, 30*b* and 30*c* (commonly referred to below as distribution channels 30). The distribution channels 30 may be normally open between process chambers 20, for example, distribution channel 30*a* is normally open between process chambers 20*a* and 20*b*. As a result, rotation of the sample processing device 10 about axis of rotation 11 will typically cause materials in the innermost process chamber 20*a* to move towards process chamber 20*b* through distribution channel 30*a*.

It should be understood that although the process arrays of the depicted sample processing devices include distribution channels between the process chambers, within the array, it may be possible to provide process arrays on devices in accord with the present invention that are connected directly with each other, i.e., the process chambers may not be separated by a distribution channel or other fluid pathway. At least some separation between process chambers within the process arrays may, however, be preferred.

Figure 4:
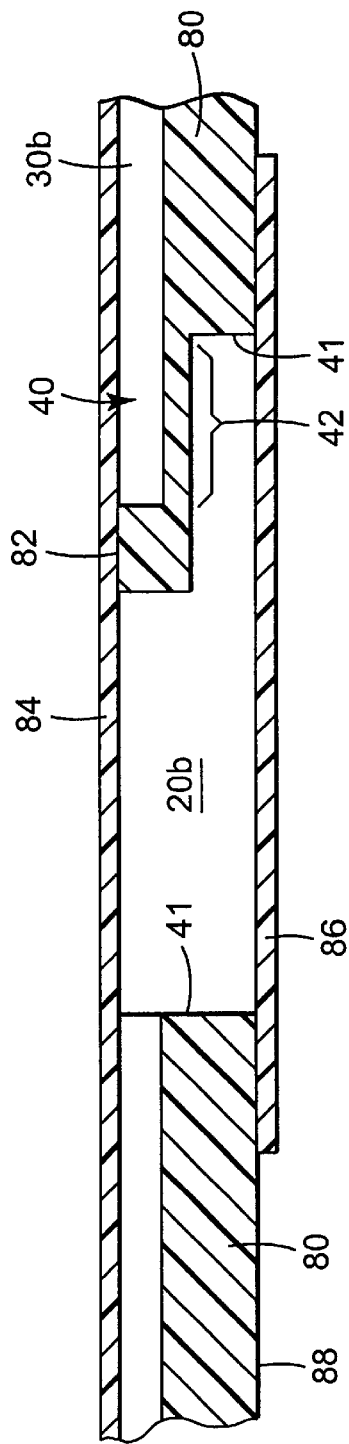
FIG. 4 is an enlarged cross-sectional view of a valved process chamber in the process array of FIG. 3 (taken along line 4—4 in FIG. 3).

FIG. 4 is a cross-sectional view of the valved process chamber 20*b* in the process array of FIG. 3 and depicts a number of other features of one potential construction of a device that could be used in connection with the present invention. The construction of the sample processing device 10 includes a core 80 in which the features of the device are formed by any suitable technique (e.g. molding, machining, etc.). One surface 82 of the core 80 may include a cover film 84 attached thereto.

The cover film 84 is typically applied along the length and width of at least each process array to seal the process chambers, distribution channels and other volumes that open to the surface 82 of the core 80. It may be preferred that the cover film 84 extend over substantially the entire surface 82 of the core 80 and, thus, be coextensive the major side seen in the plan view of, e.g., FIG. 1.

A cover film which acts as a sealing membrane, can include an adhesive, preferably, a pressure sensitive adhesive, disposed on a backing (preferably, a backing that is transparent to electromagnetic energy of selected wavelengths). The adhesive is selected such that it adheres well to materials of which conventional analytical receptacles are made (preferably polyolefins, polystyrene, polycarbonate, or combinations thereof), maintains adhesion during high and low temperature storage (e.g., about −80° C. to about 150° C.) while providing an effective seal against sample evaporation, does not substantially dissolve in or otherwise react with the components of the biological sample mixture. Thus, the type of adhesive is not critical as long as it does not interfere (e.g., bind DNA, dissolve, etc.) with any processes performed in the sample processing device 10. Preferred adhesives include those typically used on cover films of analytical devices in which biological reactions are carried out. These include poly-alpha olefins and silicones, for example, as described in International Publication Nos. WO 00/45180 (Ko et al.) and WO 00/68336 (Ko et al.).

The bottom of the process chamber 20*b* also includes a cover 86 attached to the surface 88 of the core 80 to enclose the volume of the process chamber 20*b*. Like the cover film 84, it may be preferred that the cover 86 be attached to and seal with the core 80 using an adhesive, e.g. a pressure sensitive adhesive as described herein. It may be preferred that the cover 86 be provided in the form of a metallic layer that enhances thermal energy transfer into and out of the process chamber 20*b*. In some embodiments, the cover 86 may be provided in the form of a ring-shaped structure as described in, e.g., U.S. patent application Ser. No. 09/894,810 filed on Jun. 28, 2001 and entitled ENHANCED SAMPLE PROCESSING DEVICES, SYSTEMS AND METHODS.

The process chamber 20*b* includes an integrated valve structure in the form of a lip 40 that protrudes into the periphery of the process chamber 20*b* as defined by the wall 41 which in a generally circular process chamber 20*b* extends around the entire periphery of the process chamber 20*b* (with the periphery of the process chambers 20*b* and 20*c* being depicted in a combination of solid and broken (hidden) lines in FIG. 3). It will be understood that other process chambers may have a sidewall that is broken into segments, e.g., a triangle, a square, etc.

The boundaries of the process chamber 20*b* are defined by the opening of the process chamber 20*b* onto the bottom surface 88 of the core 80. The lip 40 is in the form of an undercut extension into the volume of the process chamber 20*b* as seen in, e.g., FIG. 4. As a result, a portion of the volume of the process chamber 20*b* is located between the lip 40 and the cover 86.

A portion of the distribution channel 30*b* extends into the lip 40, with the opposite end of the distribution channel 30*b* being located in the next process chamber 20*c*. Where the distribution channel 30*b* extends onto the lip 40, an area 42 is formed with a reduced thickness relative to a remainder of the lip 40.

When an opening is provided in the lip 40 within the area 42 occupied by the distribution channel 30*b*, sample materials in the process chamber 20*b* can move into the distribution channel 30*b* for delivery to process chamber 20*c*. In the absence of an opening in the lip 40, movement of materials into process chamber 20*c* through distribution channel 30*b* is prevented by the lip 40 which otherwise seals against the cover 84 to prevent the flow of sample materials from process chamber 20*b* into the distribution channel 30*b*.

Openings in the lip 40 can be formed by any suitable technique or techniques. For example, the lip 40 may be mechanically pierced, ablated with laser energy, etc. In other embodiments, a valve structure may be incorporated in the lip 40 such that when the valve structure is opened, materials can move from the process chamber 20b into the distribution channel 30b. Examples of some valve structures may include foams, shape memory materials, etc. as described in, e.g., U.S. patent application Ser. No. 09/894,810 filed on Jun. 28, 2001 and entitled ENHANCED SAMPLE PROCESSING DEVICES, SYSTEMS AND METHODS.

The reduced thickness of the lip 40 in the area 42 occupied by the distribution channel 30b may provide a number of advantages. It may, for example, limit the location or locations in which the lip 40 may be easily pierced or otherwise deformed to provide the desired opening, i.e., the thicker portions of the lip 40 surrounding the area 42 may be more resistant to deformation by any of the techniques that could be used to form an opening therethrough. Another potential advantage of the area 42 of reduced thickness is that it can be molded into the core layer 80 along with, e.g., the process chambers and distribution channels.

Regardless of the exact nature of the valve structure used, one advantage of the process chamber with an integrated valve structure such as that depicted in FIGS. 3 and 4 is that no dead space is created between the process chamber 20b and the valve. In other words, all of the sample material located in the process chamber 20b is subjected to substantially the same conditions during processing. This could potentially not be the case if a valve were located downstream along the distribution channel 30b from the process chamber 20b. In such a situation, any sample material located in the volume of the distribution channel between the process chamber 20b and the valve could experience different conditions during processing, not receive the same exposure to reagents or other materials in the process chamber 20b, etc.

Figure 5:
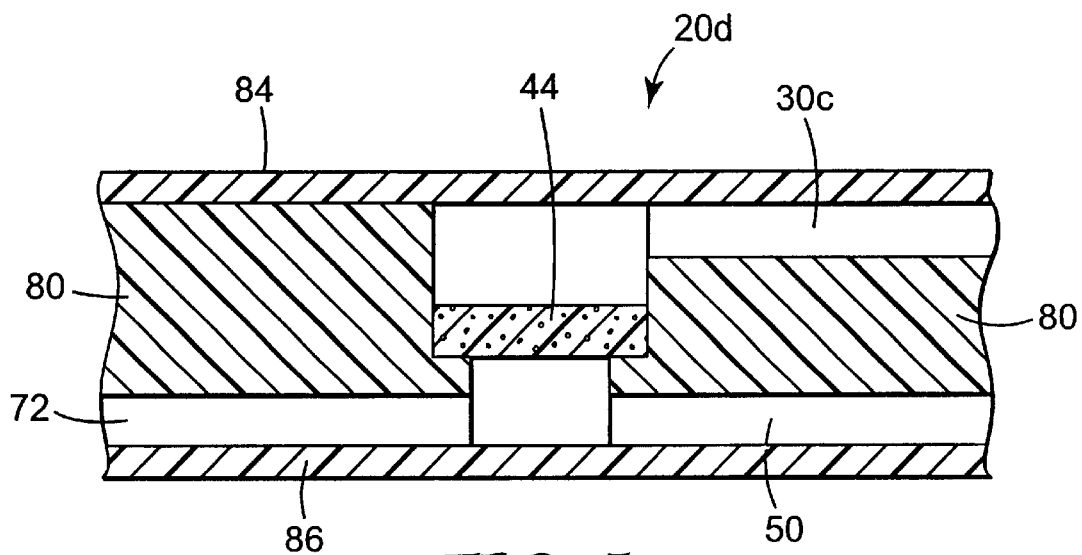
FIG. 5 is an enlarged cross-sectional view of an outermost process chamber in the process array of FIG. 3 (taken along line 5—5 in FIG. 3).

Referring now to FIG. 5, the process arrays on sample processing devices of the present invention include a connection structure located between the electrophoresis channels and at least one process chamber in the process arrays. The connection structure provides a closed configuration in which sample material is prevented from moving into the electrophoresis channel from the process array, and an open configuration in which sample material is capable of moving into the electrophoresis channel from the process array. The connection structure may take many forms, e.g., valves, membranes, etc., provided that the desired functions of controlling sample material movement into the electrophoresis channels.

In the embodiment depicted in FIG. 5, the connection structure is provided in the form of a bifurcated construction in which the process chamber 20d is separated into two separate and distinct volumes by a porous plug 44. Only materials that can pass through the porous plug 44 can move between the different portions of the process chamber 20d. The upper portion of the process chamber 20d is in fluid communication with process chamber 20c through distribution channel 30c.

The lower portion of process chamber 20d is in fluid communication with an electrophoresis medium chamber 70 (see FIG. 1) through channel 72. The lower portion of the process chamber 20d is also in fluid communication with electrophoresis channel 50. Although the channels 30c, 50, and 72 are not in the same plane and would not typically be seen in a single cross-sectional view, they are all depicted in FIG. 5 for the sake of brevity in describing the construction of the sample processing device 10.

The sample processing devices of the present invention are constructed to allow for simplified loading of the electrophoresis sieving polymers into the electrophoresis channels 50. In addition, the construction of the sample processing devices and their integral electrophoresis channels allows for the loading of electrophoresis sieving polymers in a manner that results in substantially bubble-free electrophoresis sieving polymers in the electrophoresis channels 50. To accomplish simplified, substantially bubble-free loading of the electrophoresis sieving polymers in the electrophoresis channels, the present invention relies on centrifugal forces generated by spinning the sample processing devices.

In the illustrated embodiment, the electrophoresis channel loading structure includes an electrophoresis medium chamber 70 located radially inward from the electrophoresis channel 50 (relative to the axis of rotation 11). It may be preferred that some flow restriction be provided in the electrophoresis channel 50 or in the distribution channel 72 leading from the electrophoresis medium chamber 70 to the electrophoresis channel 50 to provide sufficient back pressure during loading of the electrophoresis sieving polymers from the electrophoresis medium chamber 70 into the electrophoresis channel 50. Gas bubbles trapped in the electrophoresis sieving polymer can be driven out of the system (back towards the chamber 70) during centrifugal loading of the electrophoresis sieving polymer into the electrophoresis channel 50 when sufficient back pressure is developed as the sample processing device 10 rotates.

In the depicted sample processing device 10, the flow restriction is provided by a valve 74 located between the electrophoresis medium chamber 70 and the electrophoresis channel 50. When the sample processing device 10 is rotated with electrophoresis sieving polymer in the electrophoresis medium chamber 70 while the valve is closed, the fluid pressure generated within the electrophoresis sieving polymer is preferably sufficient to force substantially all of the bubbles out of the electrophoresis sieving polymer. After the bubbles have been removed, the valve 74 can be opened and the electrophoresis sieving polymer loaded into the electrophoresis channel 50.

The exact speed of rotation necessary to achieve that desired fluid pressure may vary depending on a variety of factors, but some suitable speeds may be about 1000 rpm or higher, potentially about 3000 rpm or higher, and in some instances about 5000 rpm or higher.

Figure 3A:
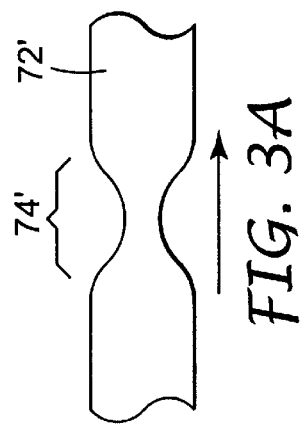
FIG. 3A depicts one exemplary flow restriction in the form of a constricted passage along a channel through which electrophoresis sieving polymer moves during loading of an electrophoresis channel.

Sufficient flow restriction may be provided, in some instances, by providing one or more constricted passages along the path of the electrophoresis sieving polymer such that the desired back pressure is generated in the electrophoresis sieving polymer as the sample processing device 10 is rotated during the loading process. One exemplary constriction is depicted in FIG. 3A where the channel 72' includes a narrowed constriction 74' in which the cross-sectional area of the channel 72' is reduced to generate the desired fluid pressure as electrophoresis sieving polymer moves in the direction of the arrow in FIG. 3A.

Although a valve and constricted passage are shown herein as illustrative examples of flow restrictors, those skilled in the art will recognize many other devices or constructions that could be substituted for a valve or constricted passage. These alternatives may include, but are not limited to, porous plugs, porous membranes, tortuous pathways, etc.

Referring to FIG. 1, for example, the electrophoresis channel 50 may preferably include an output reservoir 62 in fluid communication with the terminal chamber 60 located at the terminal end of the electrophoresis channel 50 (the end farthest from the process chamber 20*d* along the electrophoresis channel 50). The output reservoir 62 may be in fluid communication with the terminal chamber 60 through channel 63 as depicted in FIG. 1. The output reservoir 62 provides a volume for collection of any excess electrophoresis sieving polymer driven through the electrophoresis channel 50 during loading. It may be preferred that the output reservoir 62 be vented to atmosphere to facilitate complete loading of the electrophoresis channel 50. The need for venting of the output reservoir 62 may increase as the length of the electrophoresis channel 50 increases.

Rotational speeds of the sample processing devices required to obtain the desired bubble removal and full loading of the electrophoresis channels may vary depending on a variety of factors, e.g., the size of the electrophoresis channels, the viscosity of the electrophoresis sieving polymers, the geometry of the electrophoresis channels, etc. Some exemplary rotational speeds may be, e.g., about 2000 rpm or higher, in some instances about 3000 rpm or higher, and in some instances about 4000 rpm or higher. It may be beneficial to rotate the device faster during the bubble removal stage if, e.g., a flow restriction such as a valve must be opened to allow the electrophoresis sieving polymer to enter the electrophoresis channel.

Further, the loading of electrophoresis sieving polymers into electrophoresis channels 50 may be facilitated by alternately accelerating and decelerating the sample processing device 10 during rotation, essentially burping the electrophoresis sieving polymers through the electrophoresis channels 50. The rotating may be performed using at least two acceleration/deceleration cycles, i.e., an initial acceleration, followed by deceleration, second round of acceleration, and second round of deceleration. It may further be helpful if the acceleration and/or deceleration are rapid. The rotation may also preferably only be in one direction, i.e., it may not be necessary to reverse the direction of rotation during the loading process.

The actual acceleration and deceleration rates may vary based on a variety of factors such as temperature, size of the sample processing device, distance of the electrophoresis channel from the axis of rotation, materials used to manufacture the sample processing devices, properties of the electrophoresis sieving polymers (e.g., viscosity), etc.

The rotational nature of the electrophoresis sieving polymer loading process in sample processing devices of the present invention provides an advantage in that if a void or bubbles are found in the electrophoresis channels after loading with electrophoresis sieving polymer, additional rotation of the sample processing device may be used to remove the void or bubbles. In some methods of the invention, the initial rotational loading procedure may be followed by an inspection for voids or bubbles in the electrophoresis sieving polymer within the electrophoresis channels. If a void or bubbles are detected during the inspection, the sample processing device may be rotated again in an attempt to remove the void or bubbles. The secondary rotation may or may not be accompanied by the delivery of additional electrophoresis sieving polymer to the electrophoresis channels.

It may be preferred that the electrophoresis channel 50 be curved in an arc that follows the curvature of the periphery of the sample processing device 10 as seen in, e.g., FIG. 1, but the electrophoresis channel 50 may take other shapes. If the electrophoresis channel 50 is to follow the curvature of a generally circular sample processing device 10, it may extend for varying distances about the sample processing device 10. The length of the electrophoresis channel 50 may be selected based on a variety of factors, including, but not limited to, the type of separation to be performed in the electrophoresis channel 50. For example, some separations may require shorter path lengths (e.g., fragment detection, single nucleotide polymorphisms (SNP's), etc.), while other separations may require longer path lengths (e.g., de novo or gene sequencing).

One manner in which the length of the electrophoresis channel 50 may be characterized is in terms of the angular size of the arc formed by the electrophoresis channel 50 when measured relative the axis of rotation 11 about which the sample processing device 10 is rotated during use. For example, the electrophoresis channel 50 may form an arc of about 90 degrees or more, alternatively about 180 degrees or more, when measured relative the axis of rotation 11 about which the sample processing device 10 is rotated during use. It may alternatively be preferred that the electrophoresis channel 50 form a longer arc about the sample processing device 10, for example, it may be preferred that the electrophoresis channel 50 form an arc of about 320 degrees or more when measured relative the axis of rotation 11 about which the sample processing device 10 is rotated during use. Although not depicted, it should be understood that in some instances the electrophoresis channel 50 could extend more the 360 degrees about the sample processing device 10. When characterized in terms of an angular arc, the size of the sample processing device 10 will also be a factor in determining the path length of the electrophoresis channel 50.

Figure 6A:
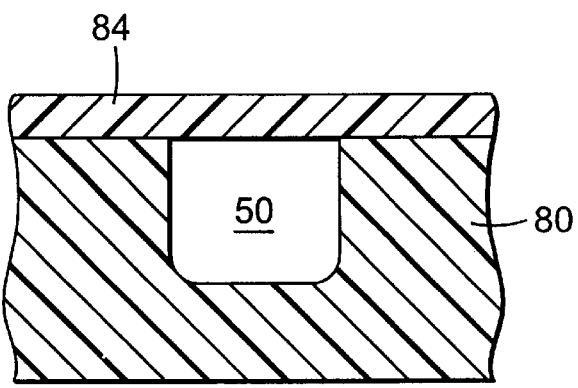
FIG. 6A is an enlarged cross-sectional view of an electrophoresis channel in the sample processing device of FIG. 1 (taken along line 6—6 in FIG. 1).
Figure 6B:
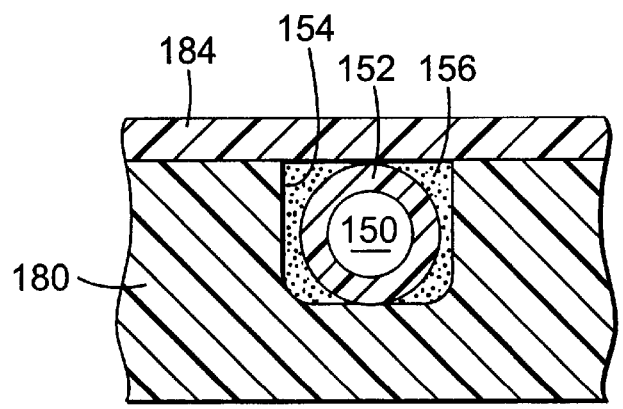
FIG. 6B is a cross-sectional view of an alternative electrophoresis channel construction.

FIGS. 6A and 6B depict cross-sectional views of alternative constructions of electrophoresis channels as used in connection with the present invention. The cross-sectional view of the electrophoresis channel 50 depicted in FIG. 6A (taken along line 6—6 in FIG. 1) shows a core 80 in which the electrophoresis channel 50 is formed as a trough by any suitable technique. The electrophoresis channel 50 is then closed by a cover film 84 attached to the core 80 by any suitable technique, e.g., adhesives, welding (thermal, chemical, etc.), etc.

Although the electrophoresis channel 50 is depicted in the cross-sectional view of FIG. 6A as having a generally rectangular or square profile, the actual profile of the electrophoresis channels used in sample processing devices of the present invention may take any suitable shape. For example, it may be desirable in some instances to provide an electrophoresis channel 50 with a more rounded bottom.

The alternative construction for an electrophoresis channel 150 seen in FIG. 6B includes a capillary or other tubing 152 located within a slot 154 formed in the core 180 of a sample processing device. The actual electrophoresis channel 150 is formed within the tubing 152, while the slot 154 is provided to hold the tubing in place.

One potential advantage of this construction is that the materials for the tubing 152 can be selected for compatibility with the electrophoresis process while the materials for the core 180 can be selected for other properties as desired. Further, it may be easier to accurately control the size of the inner diameter of the tubing 152 than to control the size of the slot 154 formed in the core 180. Another potential advantage of the construction depicted in FIG. 6B is that the size of the electrophoresis channel 150 can be varied by providing tubing 152 with a different wall thickness. As a result, a single core 180 with a slot 154 of one size may be used with tubing that has different inner diameters but the same outer diameter to provide electrophoresis channels 150 with different cross-sectional dimensions.

Another optional feature depicted in FIG. 6B is a cover film 184 located over the slot 154. The cover film 184 may be useful in retaining the tubing 152 within the slot 154 and/or protecting it from damage during use. The cover film 184 may be attached to the core 180 by any suitable technique, e.g., adhesives, welding (thermal, chemical, etc.), etc. Another option to the cover film 184 is that the tubing 152 may be retained within the slot 154 by, e.g., an adhesive such as, e.g., an optical grade epoxy.

The substrates, cover films, tubing and other components used in connection with the sample processing devices of the present invention may be manufactured of a variety of different materials, provided that the materials used are compatible with the various sample materials, reagents, etc. that may come in contact with the various materials. In addition to compatibility issues, the materials used in connection with the sample processing devices of the invention may be selected for other properties, such as transparency to electromagnetic energy of selected wavelengths, absorption of electromagnetic energy of selected wavelengths, reflectivity of electromagnetic energy of selected wavelengths, heat transfer properties, thermal mass properties, etc. For example, it may be desirable to provide fillers such as, e.g., aluminum oxide, titanium oxide, etc. in an otherwise primarily polymeric substrate to enhance selected properties of the substrate.

Further, the construction of the sample processing devices of the present invention may take on a variety of forms. Some suitable examples of different constructions for sample processing devices may be found in, e.g., U.S. patent application Ser. No. 09/894,810 filed on Jun. 28, 2001 and entitled ENHANCED SAMPLE PROCESSING DEVICES SYSTEMS AND METHODS and U.S. patent application Ser. No. 09/895,010 filed on Jun. 28, 2001 and entitled SAMPLE PROCESSING DEVICES. Other useable device constructions may be found in, e.g., U.S. Provisional Patent Application Ser. No. 60/214,508 tiled on Jun. 28, 2000 and entitled THERMAL PROCESSING DEVICES AND METHODS; U.S. Provisional Patent Application Ser. No. 60/214,642 filed on Jun. 28, 2000 and entitled SAMPLE PROCESSING DEVICES, SYSTEMS AND METHODS; U.S. Provisional Patent Application Ser. No. 60/237,072 filed on Oct. 2, 2000 and entitled SAMPLE PROCESSING DEVICES, SYSTEMS AND METHODS; U.S. Provisional Patent Application Ser. No. 60/260,063 filed on Jan. 6, 2001 and titled SAMPLE PROCESSING DEVICES, SYSTEMS AND METHODS; U.S. Provisional Patent Application Ser. No. 60/284,637 filed on Apr. 18, 2001 and titled ENHANCED SAMPLE PROCESSING DEVICES, SYSTEMS AND METHODS; and U.S. patent application Ser. No. 09/895,001 filed Jun. 28, 2001 and entitled SAMPLE PROCESSING DEVICES AND CARRIERS. Additional clean-up and/or removal materials and other features may be found in, e.g., U.S. patent application Ser. No. 10/027,226, filed Dec. 20, 2001 and entitled METHODS AND DEVICES FOR REMOVAL OF ORGANIC MOLECULES FROM BIOLOGICAL MIXTURES USING A HYDROPHILIC SOLID SUPPORT IN A HYDROPHOBIC MATRIX and in U.S. patent application Ser. No. 10/027,222, filed Dec. 20, 2001 and entitled METHODS AND DEVICES FOR REMOVAL OF ORGANIC MOLECULES FROM BIOLOGICAL MIXTURES USING ANION EXCHANGE.

Some of the devices described in connection with the above-listed references may include additional features such as, e.g., filter chambers and other methods and compositions for removal of unwanted materials from the sample mixtures, etc. The methods described herein can be used in a variety of different processes involving biological mixtures. Examples of such processes involve the clean-up of chemical reaction mixtures, e.g., nucleic acid amplification, which may or may not also be carried out in process chambers of the device. Some or all of the required reagents may be present in the device as manufactured, they may be loaded into the process chambers after manufacture of the device, they may be loaded in the process chambers just before introduction of the sample, or they may be mixed with sample before loading into the process chambers.

One method using a sample processing device according to the present invention may include starting with sample material, e.g., lysed blood cells, that are provided in a loading chamber on the device. Referring to, e.g. FIG. 1, the innermost process chamber 20a may serve as a convenient loading chamber in such a method. A filter (not shown) may preferably be provided to filter the starting sample material as it moves from the loading chamber 20a to the next process chamber 20b through distribution channel 30a. Movement or transfer of the sample materials from the loading chamber 20a to the process chamber 20b may preferably be accomplished by rotating the sample processing device 10 about the axis of rotation 11.

The process chamber 20b may preferably include suitable polymerase chain reaction (PCR) primers as supplied, e.g., dried down in each of the chambers 20b. Each of the chambers 20b may include the same primer or different primers depending on the nature of the investigation being performed on the starting sample material. One alternative to providing the primers in the process chambers before loading the sample is to add a suitable primer to the loading chamber 20a with the starting sample material (provided that the primer is capable of passing through the filter, if present).

After locating the starting sample material and any required primers in the process chambers 20b, the biological mixtures in the process chambers 20b are thermally cycled under conditions suitable for PCR amplification of the selected genetic material. Such thermal cycling may preferably occur while the sample processing device 10 is rotated as described in some of the references identified above.

Rotation of any sample processing device 10 during the PCR process (or at any other desired time) may be used to facilitate mixing through mechanical agitation of the sample materials and any other materials (e.g., reagents, etc.) present in the process chambers. The mechanical agitation may be accomplished by oscillating the sample processing device 10 in opposite directions about the axis of rotation 11. The oscillations may vary in frequency and/or magnitude depending on a variety of factors, e.g., the size/shape of the process chambers, the amount of materials in the process chambers, viscosities, temperatures, stability of the sample materials, etc. For example, it may be useful to accomplish mixing by oscillating the sample processing device 10 at a frequency of about 1 Hertz to about 100 Hertz. The magnitude of the oscillations may be, e.g., from about 5 degrees to about 360 degrees.

The mechanical agitation can be carried out during, for example, PCR, Sanger cycling, clean-up of the PCR reaction mixture, clean-up of the sequencing reaction mixture, as well as during various other processes that can be carried out in the microfluidic sample processing devices described herein. Similarly, mechanical agitation by rotation, or other technique, can be carried out on any of the sample processing devices described herein.

After completion of the PCR amplification process, the materials in each of the process chambers 20b may be moved through another filter chamber (not shown), with one filter chamber being provided for each process chamber 20b to remove unwanted materials from the amplified materials in the biological mixture, e.g., PCR primers, unwanted materials in the starting sample that were not removed by filter or filters, etc. In some instances, the process chambers 20 and/or distribution channels 30b may include active chemistries coated on surfaces. Alternatively, or additionally, they may contain the solid-phase materials for sample clean-up (e.g., dye removal). The area in which the active chemistry is included in such devices can be a process chamber 20 or in the volume defined by a connection between two process chambers or both.

The PCR amplification products from each of the process chambers 20b are moved into process chambers 20c for, e.g., sequence cycling of the genetic materials amplified in process chambers 20b through appropriate control of the thermal conditions encountered in process chambers 20c. It may, however, be preferred to clean-up the sample materials before performing any desired processes in process chambers 20c by, e.g., passing the sample materials through a filter chamber, etc.

After completion of the sequence cycling (e.g., Sanger sequencing) process in process chambers 20c, the materials in each of the process chambers 20c may be moved into the outermost process chambers 20d by, e.g., opening a valve and rotating the sample processing device 10 about the axis of rotation 11. It may be preferred to pass the sequence cycling reaction products through, e.g., another filter chamber (not shown) to remove unwanted materials from the sequencing ladders (e.g., sequencing primers, ddNTPs, etc.). The filter chambers may, e.g., contain active chemistry coated on surfaces of the chamber, for example. Alternatively, or additionally, they may contain solid-phase materials for sample clean-up (e.g., dye removal).

After moving the sample materials into the outermost process chamber 20d, the target DNA materials in the sample can be moved into the electrophoresis channel 50 by any number of techniques. Typically, however, the electrophoresis channel 50 will be separated from the process chamber 20d by, e.g., a porous plug 44 or other barrier that can prevent flow of the electrophoresis sieving polymers into the process chamber 20d during loading of the electrophoresis channel 50 and also prevent the passage of unwanted materials from the process chamber 20d into the electrophoresis channel 50.

One technique that can be used to move the target DNA materials through the porous plug and into the electrophoresis channel 50 is electrokinetic injection. For example an electrode located within the process chamber 20d could be used in connection with a second electrode located within the electrophoresis channel 50. By applying the appropriate voltages to the electrodes, the target DNA material within the process chamber 20d can be moved through the porous plug and into the electrophoresis channel 50 where separation can occur. Other potentially suitable techniques that could be used in place of electrokinetic injection through a porous plug include, but are not limited to, hydraulic loading, valving, etc.

The actual techniques of performing sequencing separations in the electrophoresis channel 50 are substantially similar to the techniques used when performing sequencing separations using conventional equipment, devices and techniques. For example, a first electrode 56 may be provided in electrical communication with the electrophoresis sieving polymer in the electrophoresis channel 50 proximate the process chamber 20d. The first electrode 56 may be attached to the sample processing device 10 such that it forms an integral part of the device 10, or it may be provided separately as, e.g., a probe inserted into the electrophoresis channel 50 proximate the process chamber 20d. The exact construction and/or form of the electrode will be known to those skilled in the art of electrophoresis separation methods.

A second electrode 58 may be provided distal from the first electrode that is located proximate the process chamber 20d from which the target DNA enters the electrophoresis channel 50. The second electrode 58 may also be attached to the sample processing device 10 such that it forms an integral part of the device 10, or it may be provided separately as, e.g., a probe inserted into the electrophoresis channel 50 proximate the terminal chamber 60 located at the opposite end of the electrophoresis channel 50 from the process chamber 20d. By applying the appropriate voltages to the electrodes 56 and 58 in the electrophoresis channel 50, the target DNA material within the electrophoresis channel 50 can be separated as desired.

Figure 7:
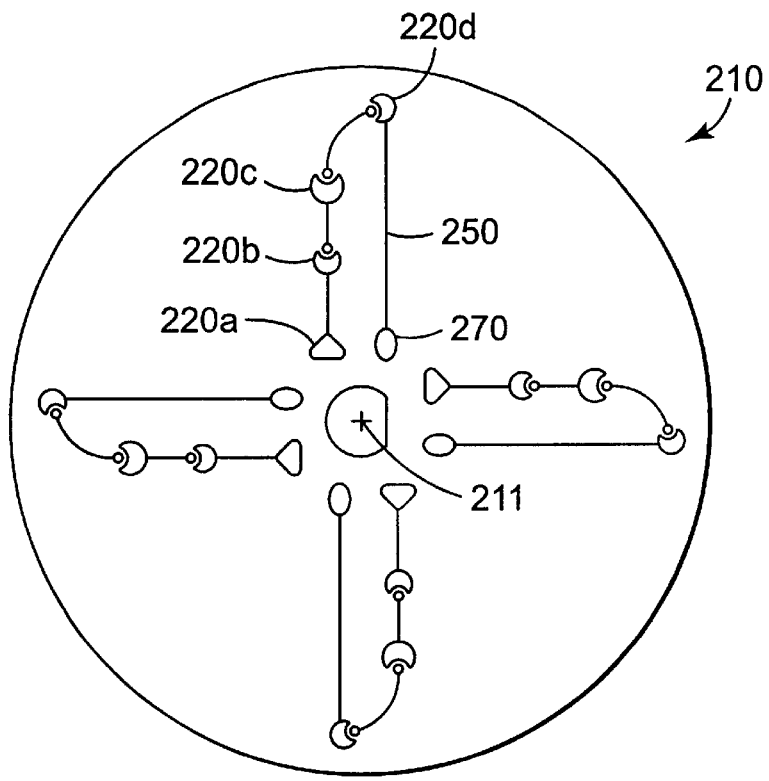
FIG. 7 is a plan view of an alternative sample processing device according to the present invention.

An alternative sample processing device 210 is depicted in FIG. 7 and includes process arrays including process chambers 220a, 220b, 220c, and 220d and connecting distribution channels connecting the process chambers in sequence. The arrangement of process chambers and distribution channels is similar to that described above in connection with the sample processing device 10 illustrated in FIGS. 1 and 2.

One significant difference, however, is that the electrophoresis channels 250 on the sample processing device 210 are not curved in an arc as are the electrophoresis channels 50 of sample processing device 10. It may be preferred that the electrophoresis channels 250 be arranged radially on the device 210. It may further be preferred, but not required, that the electrophoresis channels 250 be generally straight as seen in FIG. 7.

In the configuration shown in FIG. 7, the electrophoresis channels 250 may not require any venting proximate the outermost end of the electrophoresis channel 250 (i.e., the end located furthest from the axis of rotation 211) to provide for complete loading of the channels with electrophoresis sieving polymers. As discussed below, the electrophoresis channels may be unvented. In such a situation, however, it may be desirable to employ a variety of acceleration/deceleration profiles to facilitate complete and substantially bubble-free loading of the electrophoresis channels 250.

Furthermore, when the electrophoresis channels are unvented, a flow restriction (e.g., a valve or constricted passage) may not be required to assist with bubble removal from the electrophoresis sieving polymer during loading. The unvented nature of the electrophoresis channels 250 may allow for the generation of fluid pressure within the electrophoresis sieving polymer during loading to remove bubbles and/or voids in the electrophoresis sieving polymer.

Figure 8:
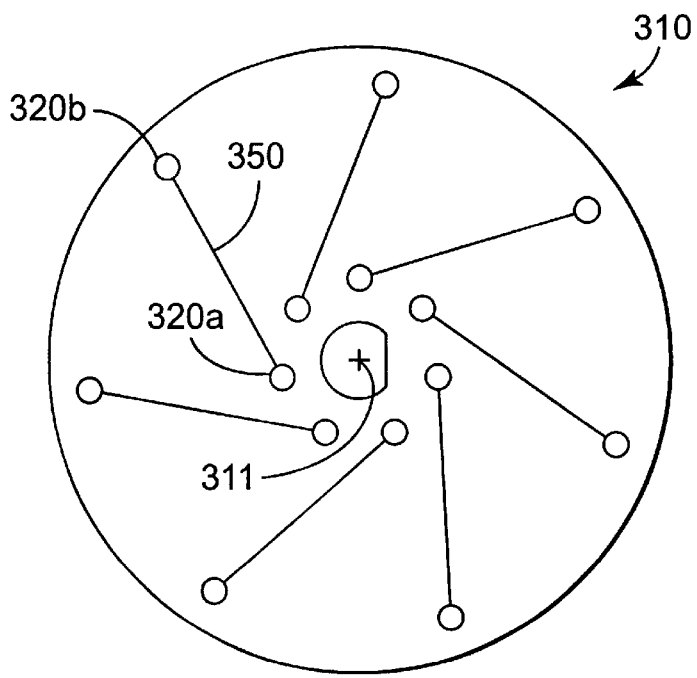
FIG. 8 is a plan view of an alternative sample processing device according to the present invention.

Another illustrative variation in the sample processing devices of the present invention is depicted in FIG. 8, in which a sample processing device 310 includes a number of electrophoresis channels 350 arranged such that they include an inner process chamber 320a located proximate the axis of rotation 311 and an outer process chamber 320b located further away from the axis of rotation 311 than the inner process chamber 320a. As a result, materials located within inner process chamber 320a can be loaded in the electrophoresis channels 350 by rotation of the sample processing device 310 about the axis of rotation 311. Although the electrophoresis channels 350 are not located along geometrically accurate radial lines, the electrophoresis channels 350 will be considered to be arranged "generally radially" for the purposes of the present invention. It will be understood that in the simpler construction depicted in FIG. 8, the inner process chamber 320a can function as both the entry point for the electrophoresis sieving polymer (i.e., the process chamber functions as the electrophoresis medium chamber), as well as the entry point for the sample materials to be processed using the electrophoresis channels 350.

Figure 9:
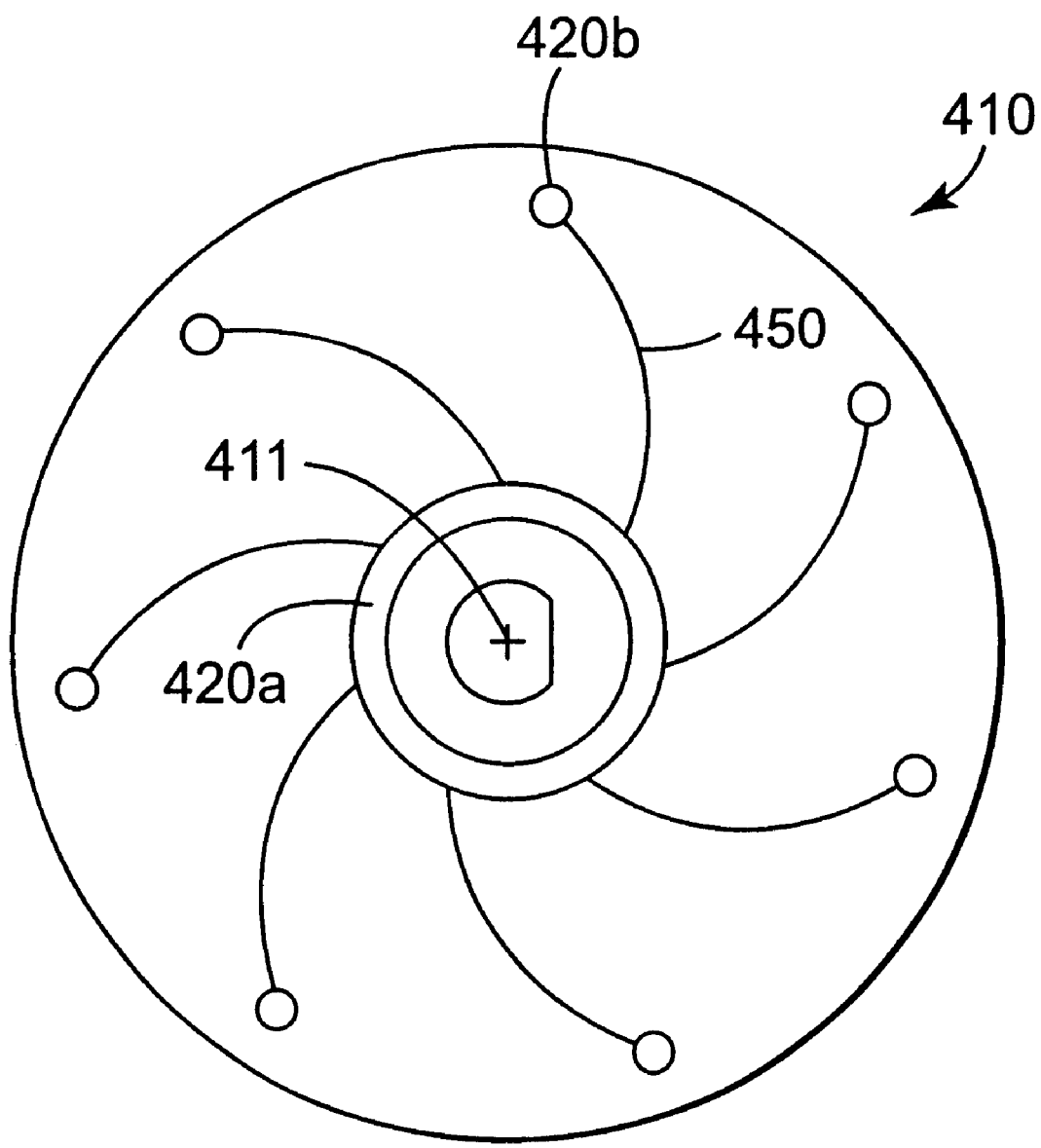
FIG. 9 is a plan view of an alternative sample processing device according to the present invention.

FIG. 9 depicts another alternative sample processing device 410 according to the present invention. The sample processing device 410 includes a plurality of electrophoresis channels 450 extending generally radially outward from the axis of rotation 411 of the sample processing device 410. Each of the electrophoresis channels 450 emanates from a central process chamber 420a provided in the shape of a ring and terminates in a process chamber 420b.

All of the electrophoresis channels 450 are in fluid communication with the single process chamber 420a, although it should be understood that in sample processing devices of the present invention two or more process chambers could be provided in place of the single process chamber 420a, with each of the two or more process chambers being in fluid communication with two or more of the electrophoresis channels 450.

As with FIG. 8, it will be understood that in the simpler construction of FIG. 9, the inner process chamber 420a can function as both the entry point for the electrophoresis sieving polymer (i.e., the process chamber functions as the electrophoresis medium chamber), as well as the entry point for the sample materials to be processed using the electrophoresis channels 450.

As discussed above, the electrophoresis channels depicted in connection with FIGS. 1 and 2 are preferably vented proximate their terminal ends (i.e., the ends distal from the electrophoresis medium chambers) to facilitate complete filling of the electrophoresis channels with electrophoresis sieving polymers. In contrast, the shorter electrophoresis channels depicted in connection with, e.g., FIGS. 7–9 may not need to be vented proximate their terminal ends to obtain complete filling of the electrophoresis channels. In other words, the electrophoresis channels on the devices 310 and 410 can be unvented, with the only openings into and out of the electrophoresis channels being located proximate the electrophoresis medium chambers or process chambers used to load materials into the electrophoresis channels. If the electrophoresis channels are unvented, the use of multiple acceleration/deceleration profiles discussed above may be used to facilitate complete filling of the unvented electrophoresis channels.

Patents, patent applications, and publications disclosed herein are hereby incorporated by reference (in their entirety) as if individually incorporated. It is to be understood that the above description is intended to be illustrative, and not restrictive. Various modifications and alterations of this invention will become apparent to those skilled in the art from the foregoing description without departing from the scope of this invention, and it should be understood that this invention is not to be unduly limited to the illustrative embodiments set forth herein.

What is claimed is:

1. A method of providing an electrophoresis channel containing an electrophoresis sieving polymer, the method comprising:

providing a device comprising a plurality of electrophoresis channels and at least one electrophoresis medium chamber;

providing electrophoresis sieving polymer in the at least one electrophoresis medium chamber; and rotating the device about an axis of rotation while the at least one electrophoresis medium chamber is in fluid communication with each electrophoresis channel of the plurality of electrophoresis channels, wherein the at least one electrophoresis medium chamber is located radially inward from the plurality of electrophoresis channels relative to the axis of rotation;

wherein the electrophoresis sieving polymer in the at least one electrophoresis medium chamber moves into the plurality of electrophoresis channels during the rotating.

2. A method according to claim 1, wherein the plurality of electrophoresis channels are arranged generally radially with respect to the axis of rotation.

3. A method according to claim 1, wherein at least a portion of the rotating is performed while preventing movement of the electrophoresis sieving polymer into at least one electrophoresis channel of the plurality of electrophoresis channels.

4. A method according to claim 3, wherein the preventing comprises holding a valve in a closed configuration between the at least one electrophoresis medium chamber and the at least one electrophoresis channel.

5. A method according to claim 4, further comprising opening the valve between the at least one electrophoresis medium chamber and the at least one electrophoresis channel, wherein the electrophoresis sieving polymer moves into the at least one electrophoresis channel.

6. A method according to claim 1, further comprising:
   inspecting the plurality of electrophoresis channels for gas bubbles in the electrophoresis sieving polymer within the plurality of electrophoresis channels after rotating the device; and
   rotating the device about the axis of rotation after inspecting if the inspecting reveals gas bubbles.

7. A method according to claim 1, wherein the rotating comprises at least two acceleration/deceleration cycles.

8. A method according to claim 1, wherein the electrophoresis sieving polymer moves in a generally radial direction relative to the axis of rotation when the electrophoresis sieving polymer in the at least one electrophoresis medium chamber moves into the plurality of electrophoresis channels during the rotating.

9. A method of providing an electrophoresis channel containing an electrophoresis sieving polymer, the method comprising:

providing a device comprising at least one electrophoresis medium chamber and a plurality of electrophoresis channels, wherein each electrophoresis channel of the plurality of electrophoresis channels comprises an unvented electrophoresis channel;

providing electrophoresis sieving polymer in the at least one electrophoresis medium chamber; and rotating the device about an axis of rotation while the at least one electrophoresis medium chamber is in fluid communication with each electrophoresis channel of the plurality of electrophoresis channels, wherein the at least one electrophoresis medium chamber is located radially inward from the plurality of electrophoresis channels relative to the axis of rotation;

wherein the electrophoresis sieving polymer in the at least one electrophoresis medium chamber moves into the plurality of electrophoresis channels during the rotating.

10. A method according to claim 9, wherein the plurality of electrophoresis channels are arranged generally radially with respect to the axis of rotation.

11. A method according to claim 9, further comprising rotating the sample processing device while preventing movement of the electrophoresis sieving polymer into at least one electrophoresis channel of the plurality of electrophoresis channels.

12. A method according to claim 11, wherein the preventing comprises holding a valve in a closed configuration between the at least one electrophoresis medium chamber and the at least one electrophoresis channel.

13. A method according to claim 12, further comprising opening the valve between the at least one electrophoresis medium chamber and the at least one electrophoresis channel, wherein the electrophoresis sieving polymer moves into the at least one electrophoresis channel.

14. A method according to claim 9, further comprising:
inspecting the plurality of electrophoresis channels for gas bubbles in the electrophoresis sieving polymer within the plurality of electrophoresis channels after rotating the device; and
rotating the device about the axis of rotation after inspecting if the inspecting reveals gas bubbles.

15. A method according to claim 9, wherein the rotating comprises at least two acceleration/deceleration cycles.

16. A method according to claim 9, wherein the electrophoresis sieving polymer moves in a generally radial direction relative to the axis of rotation when the electrophoresis sieving polymer in the at least one electrophoresis medium chamber moves into the plurality of electrophoresis channels during the rotating.

* * * * *